(12) United States Patent
Kuiken

(10) Patent No.: US 7,922,773 B1
(45) Date of Patent: Apr. 12, 2011

(54) METHOD AND APPARATUS FOR PROSTHETIC LIMB ROTATION CONTROL

(75) Inventor: Todd A. Kuiken, Oak Park, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 148 days.

(21) Appl. No.: 12/466,872

(22) Filed: May 15, 2009

Related U.S. Application Data (60) Provisional application No. 61/053,865, filed on May 16, 2008.

(51) Int. Cl.
A61F 2/48 (2006.01)
A61F 2/60 (2006.01)
A61F 2/54 (2006.01)

(52) U.S. Cl. ............... 623/24; 623/33; 623/58

(58) Field of Classification Search ............ 623/24, 623/38, 57–653
See application file for complete search history.

(56) References Cited

U.S. PATENT DOCUMENTS

| 5,507,835 A * | 4/1996 | Jore ........................... 623/36 |
| 6,273,918 B1 * | 8/2001 | Yuhasz et al. ................ 623/33 |
| 2006/0293762 A1 * | 12/2006 | Schulman et al. ............ 623/32 |
| 2009/0254196 A1 * | 10/2009 | Cox et al. ..................... 623/33 |
| 2010/0234967 A1 * | 9/2010 | Whiteley et al. .............. 623/24 |

OTHER PUBLICATIONS

Li et al., "Modeling of Prosthetic Limb Rotation Control by Sensing Rotation of Residual Arm Bone," *IEEE Transactions on Biomedical Engeering*, 55 (9): 2134-2142, Sep. 2008.
Rouse, "Algorithm development for sensing the position and orientation of a magnet within residual bone," Northwestern University, Jun. 2009.
Nahlik, "Development of osseo-magnetic link for intuitive rotational control of upper limb prostheses," Northwestern University, Jun. 2009.

* cited by examiner

*Primary Examiner* — Bruce E Snow
(74) *Attorney, Agent, or Firm* — Drinker Biddle & Reath LLP (57) ABSTRACT

A method and apparatus for improving the control of prosthetic limb rotation in amputees in which a permanent magnet is implanted into the distal end of a residual bone and the bone rotation is sensed from movement of the magnetic field of the magnet and used to effect corresponding rotation of the prosthetic limb.

19 Claims, 6 Drawing Sheets

METHOD AND APPARATUS FOR PROSTHETIC LIMB ROTATION CONTROL

CROSS-REFERENCE TO RELATED PATENT APPLICATIONS

This patent application claims the benefit of U.S. Provisional Patent Application No. 61/053,865, filed May 16, 2008.

FIELD OF THE INVENTION

This invention pertains generally to motorized prostheses and, more particularly, to a motorized prosthetic limb for attachment to a residual bone to instantaneously convert residual bone rotation into prosthetic limb rotation.

BACKGROUND OF THE INVENTION

Limb rotation is valuable—if not essential—for performing daily tasks. For example, forearm and humeral rotations are important motions employed in virtually all activities of daily living and are essential motions for controlling upper limb prostheses. Femoral rotation is not typically provided for lower limb prostheses, but if available, would allow lower limb amputees to more easily perform activities such as dressing or transferring in and out of vehicles. Currently, passive devices constitute the majority of commercially available prosthetic rotators. Passive control is achieved by manually positioning the devices or by manipulating the devices against a stable object.

Body-powered and myoelectric wrist rotators are also available, but are fitted much less frequently. Body-powered control uses biscapular abduction to control the rotator through tensioning a cable system, and allows the user to lock the wrist or humeral rotator in various positions. Myoelectric control is based on measurements of electromyogram (EMG) signals of agonist-antagonist muscle pairs to control a motorized prosthetic rotator. Both active control methods operate all components sequentially and utilize muscles that do not necessarily relate to arm rotation. As a result, the rotational control of the arm is slow, unnatural, and cannot maintain inherent proprioceptive awareness of limb rotation. Since the amputees cannot feel the orientation of their prosthesis, they must use visual feedback to determine how their artificial limb is positioned in space. This lack of proprioceptive feedback impedes prosthetic control, increases the cognitive burden of using a prosthesis and impairs functions in all applications.

The only available mechanisms of femoral rotation available to lower limb amputees are passive femoral rotators, and they are rarely prescribed. Existing upper limb prosthetic rotators have not been adapted for rotation of lower limb prostheses because lower limb prostheses are all passively controlled; there is currently no analog in the lower limb to body-powered or myoelectric control in the upper limb. Therefore, even if such a device were available, the amputee would have no way to control it.

One known method to improve voluntary control of prosthesis rotation is to physically couple the rotation of the bones remaining in the residual limb to the prosthesis rotation. For example, two interfacing mechanisms have been developed to create a physical connection between the residual humerus and the prosthesis for control of the prosthesis rotation, osseointegration and artificial epicondyles. Osseointegration is a direct structural connection between residual bone and the prosthesis. This technique involves implanting a titanium bolt into the bone of the residual limb. An abutment attaches to the bolt and protrudes through the skin to provide direct attachment to the prosthesis so that the manipulation of the prosthesis including prosthesis rotation follows movement of the bone. Another attachment method is the use of artificial epicondyles that are created by surgically inserting an implant into the residual bone and covering the implant with soft tissue and skin. The artificial epicondyles can suspend the prosthesis and provide the function of rotation of the prosthesis.

Patients using such systems employing osseointegration and artificial epicondyles have rotation control with preservation of proprioception for rotation of their artificial limb in the longitudinal axis of the residual limb. However, these approaches have significant drawbacks. For example, direct skeletal attachment may give rise to infections at the skin interface and the implants may loosen over time. Also, loading of the skin over artificial epicondyles can cause skin breakdown and there is similarly a potential for loosening of the implants. Both systems require extensive surgical procedures and significantly delay use of the prosthesis as the implants integrate with the residual bone matrix.

The present invention provides improved rotational control of prostheses while avoiding the significant drawbacks of systems employing osseointegration and artificial epicondyles. Also, since the present invention instantaneously converts residual bone rotation into prosthetic limb rotation, it maintains inherent proprioceptive awareness of limb rotation reducing the cognitive burden of the use of the prosthesis while insuring accurate and natural rotation. Finally, the improved rotational control of the present invention will not compromise other applicable control sources, such as biceps and triceps EMG that can be used to operate other degrees of freedom such as wrist and hand movements. Therefore, the present invention can be readily combined with other prosthesis controls to achieve additional prosthesis functionality.

SUMMARY OF THE INVENTION

The invention comprises a prosthetic limb for instantaneously converting residual bone rotation into rotation of a portion of a prosthetic limb. The prosthetic limb may be a residual humerus in which case the prosthetic limb portion will be a prosthetic arm. Alternatively, the prosthetic limb may be a residual radius in which case the limb portion will be a prosthetic wrist and hand. Finally, the prosthetic limb may be a femur in which case the limb portion will be a femoral portion above the knee.

In accordance with the invention, a permanent magnet having a magnetic field is attached adjacent to the distal end of the rigid bone. A plurality of magnetic sensors are disposed about the magnet for generating data indicative of changes in the magnetic field produced by rotation of the residual bone and magnet. A motor driven prosthetic rotator is also provided for rotating the limb portion. Finally, the prosthetic limb includes a microprocessor programmed to analyze the data indicative of the changes in the magnetic field and to control the prosthetic rotator in response to that data. In this way, the residual bone rotation is converted into rotation of the limb portion.

Preferably, the magnet will be disposed of with its magnetic axis perpendicular to the longitudinal axis of the residual bone. The magnet may be hermetically sealed in a titanium metal casing with self-tapping threads formed along the cylindrical outer surface of the casing. This threaded titanium casing can then be screwed into a bore formed in the residual bone in order to attach the magnet to the bone.

In a preferred embodiment of the invention the sensors are arranged in clusters of three orthogonally disposed sensors. The orthogonally arranged sensors are aligned to measure the magnetic field along the orthogonal X, Y, and Z axes. Also the X axis is preferably aligned with the longitudinal axis of the residual limb.

Finally, the prosthetic limb may be provided with a shield cap made from a high magnetic permeability material in order to avoid interference from magnetic devices in proximity to the prosthetic limb. The shield cap will be positioned to contain the magnet and magnetic sensors of the prosthetic limb.

BRIEF DESCRIPTION OF THE DRAWINGS

In order to aid in understanding the invention, it will now be described in connection with exemplary embodiments thereof with reference to the accompanying drawings in which like numerical designations will be given to like features with reference to the accompanying drawings wherein.

DETAILED DESCRIPTION OF PREFERRED EMBODIMENTS OF THE INVENTION

The embodiments of the invention described in detail below are not intended to be exhaustive or to limit the invention to the precise structure and operation disclosed. Rather, the described embodiments have been chosen and described to explain the principles of the invention and its application, operation and use in order to best enable others skilled in the art to follow its teachings.

Figure 1:
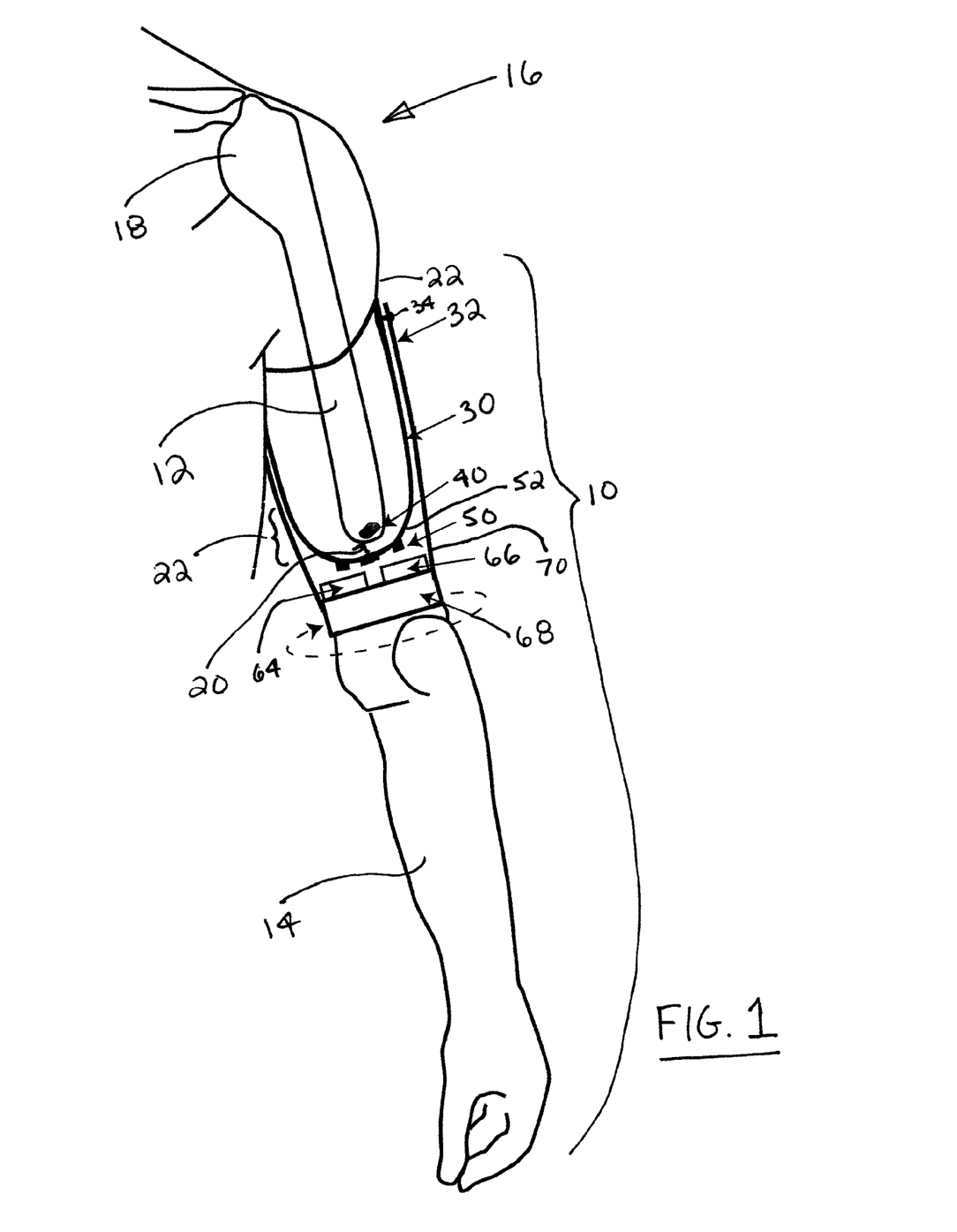
FIG. 1 is a diagrammatic representation of a superior limb prosthesis in accordance with the invention attached to a residual humerus.

Turning now to FIG. 1, a superior limb prosthesis 10 for instantaneously converting rotation of the residual humerus 12 into rotation of a prosthetic arm (or forearm) 14 is depicted diagrammatically. Humeral rotation is caused by the shoulder girdle muscles (not expressly depicted but generally present in the shoulder complex region 16) acting on the proximal humerus 18.

Humeral rotation produces arm rotation in able-bodied people as the distal humerus (or condyle) causes the lower arm to turn. Transhumeral amputees can fully rotate their humeri like able-bodied people and can feel the rotation angle and where their lost arm would be pointing. This is due to the proprioceptive elements in the shoulder complex region which provide feedback from muscle spindles, golgi tendon organs, joint capsule afferents and other inputs. However, in arm amputees humeral rotation does not translate into arm rotation. This is because, although the skin covering the distal end of the residual humerus is fixed in the prosthetic socket, the residual humerus simply rotates in its compliant soft tissue envelope producing little or no prosthetic arm rotation.

Thus, as illustrated in FIG. 1, the distal end 20 of residual humerus 12 is covered by a layer of skin 22 including a subcutaneous fat layer (not shown) which extends over the distal end of the residual humerus. The skin layer forms a compliant soft tissue envelop 22 within which the amputee will rotate the humerus to operate the superior limb prosthesis.

In order to attach the superior limb prosthesis, an inner socket 30 is fit intimately to the residual limb. Then an outer socket 32 is mechanically attached to the inner socket such as with bolts 34 or by other conventional attachment means. Mechanical and electrical parts of the prosthesis are mounted in the outer socket as will be described below. Also, a suspension sleeve or liner typically made of an elasticized or elastomeric material such as silicone (not shown) often will be included at the interface of the inner socket and the skin covering the distal end of the residual limb.

Figure 1A:
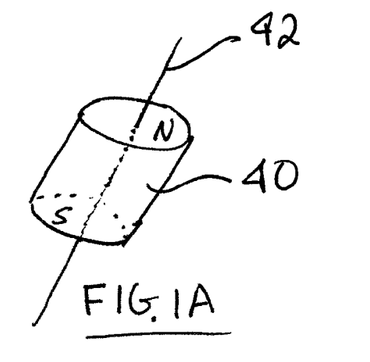
FIG. 1A depicts a cylindrical magnet that may be used in the present invention and FIG. 1B depicts a titanium shield hermitically sealing the magnet.

A permanent magnet 40 with a fixed magnetic field is attached and preferably centered in the bone adjacent distal end 20 of the humerus. While magnet 40 may be made of generally any permanent magnetic material, currently neodymium magnets (which contain iron, boron, and the rare-earth element neodymium) are preferred. The magnet may be of any desired shape, although currently cylindrical magnets like that depicted in FIG. 1A are preferred. Taking the "magnetic axis" 42 as a line drawn between centers of the opposite magnetic poles of the magnet, it is preferred that the magnetic axis of magnet 40 be perpendicular to the longitudinal axis of the residual humerus in which it is mounted. However, the magnetic axis may be oriented coaxially with the longitudinal axis of the residual bone if desired, since the algorithm responsible for processing the magnetic field data may be adjusted to accommodate differing orientations of the magnetic field of the magnet.

Figure 1B:
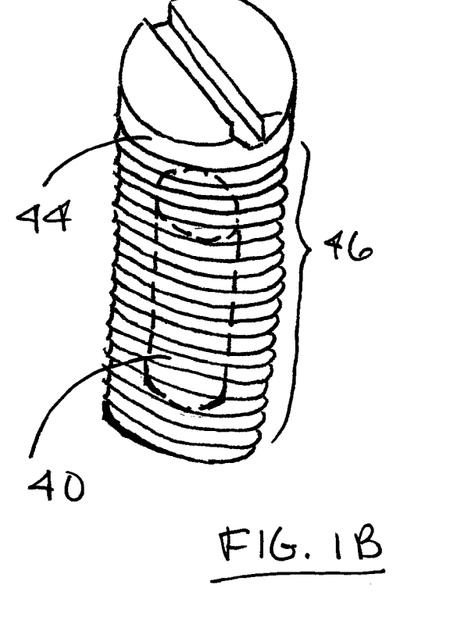

In order to facilitate the installation of magnet 40 in the distal end of residual humerus 12, it is preferred that the magnet be hermetically sealed in a titanium metal casing. Titanium is preferred because it is a known biocompatible material and it will not interfere with the magnetic field of the permanent magnet. This is illustrated in FIG. 1B where cylindrical magnet 40 is shown in broken lines positioned within a titanium casing 44 and self-tapping threads 46 are formed along the cylindrical outer surface of the casing so that the magnet can be easily secured into the bone much like conventional self-tapping orthopedic screws.

The installation of the threaded titanium casing is simple and straightforward. First, a small incision is made in the skin covering the humerus at the site where the magnet is to be installed, preferably spaced back from the distal tip 48 of the residual humerus as little as possible but a sufficient distance to avoid overstressing and thereby endangering the distal bone structure. Then a hole is bored with an appropriate diameter to receive the threaded titanium casing holding magnet 40. The bore should be deep enough to insure that the casing does not protrude from the surface of the humerus. Next, the threaded titanium casing is screwed home to center it in the bone and the wound is closed. Once the magnet is in place, its magnetic field will be fixed with respect to the residual humerus. Thus, when the amputee rotates the residual radius, magnet 40 will rotate with the residual bone. In transradial amputees, the magnet will be located in the distal end of the radius and in transfemoral amputees, the magnet will be mounted in the femur above the knee.

The next component of the superior limb prosthesis is a matrix of two or more magnetic sensors 50 that are disposed in the prosthesis about magnet 40 to sense the rotation of the magnetic field of magnet 40 as the amputee rotates residual humerus 12 within compliant soft tissue envelop 22. The rotation of the residual humerus shifts the position of the magnetic field of the magnet that is detected by magnetic sensors 40. As shown in FIG. 1, magnetic field sensors 50 are mounted to the outer surface 52 of inner socket 30. Although the sensors are shown diagramatically as protruding from the outer surface of the socket, they may be embedded in the wall of the socket so long as they do not protrude or disrupt the smooth even inner surface of the socket. The sensors should be fixed in place so that they do not move with respect to each other and they also should be evenly distributed about the magnet in the assembled and deployed superior limb prosthesis. It is currently preferred that the sensors lie in a single plane that is oriented perpendicularly to the longitudinal axis of the residual bone although non-coplanar configurations may be used.

Figure 2A:
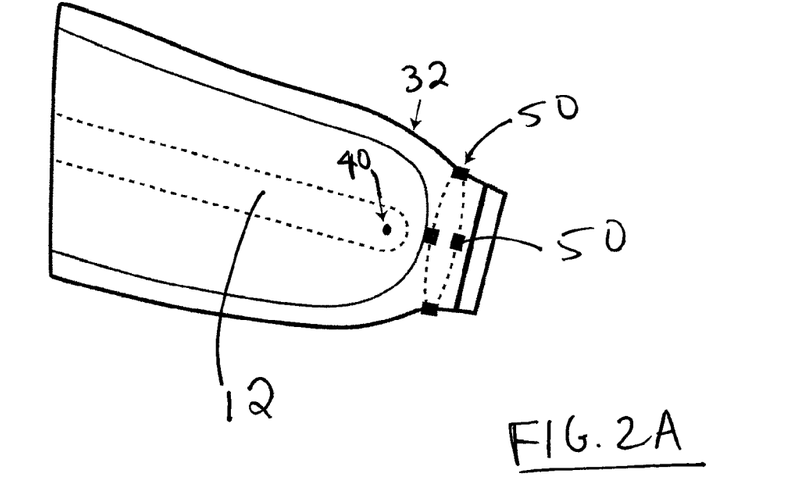
FIGS. 2A and 2B diagrammatically represent relative positioning between the magnet and the plane of four magnet sensors positioned in accordance with the present invention.
Figure 2B:
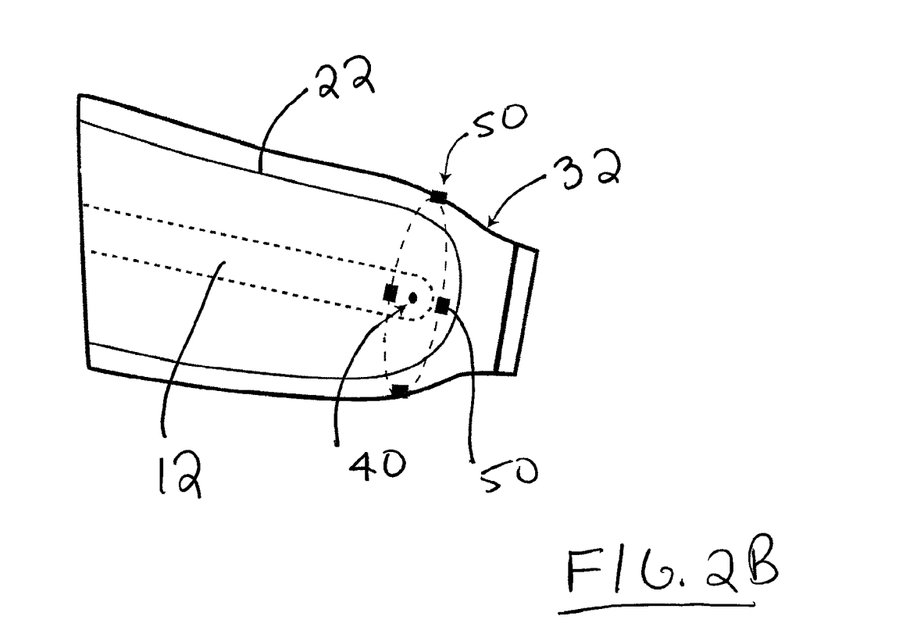
Figures 3A, 3B, 3C:
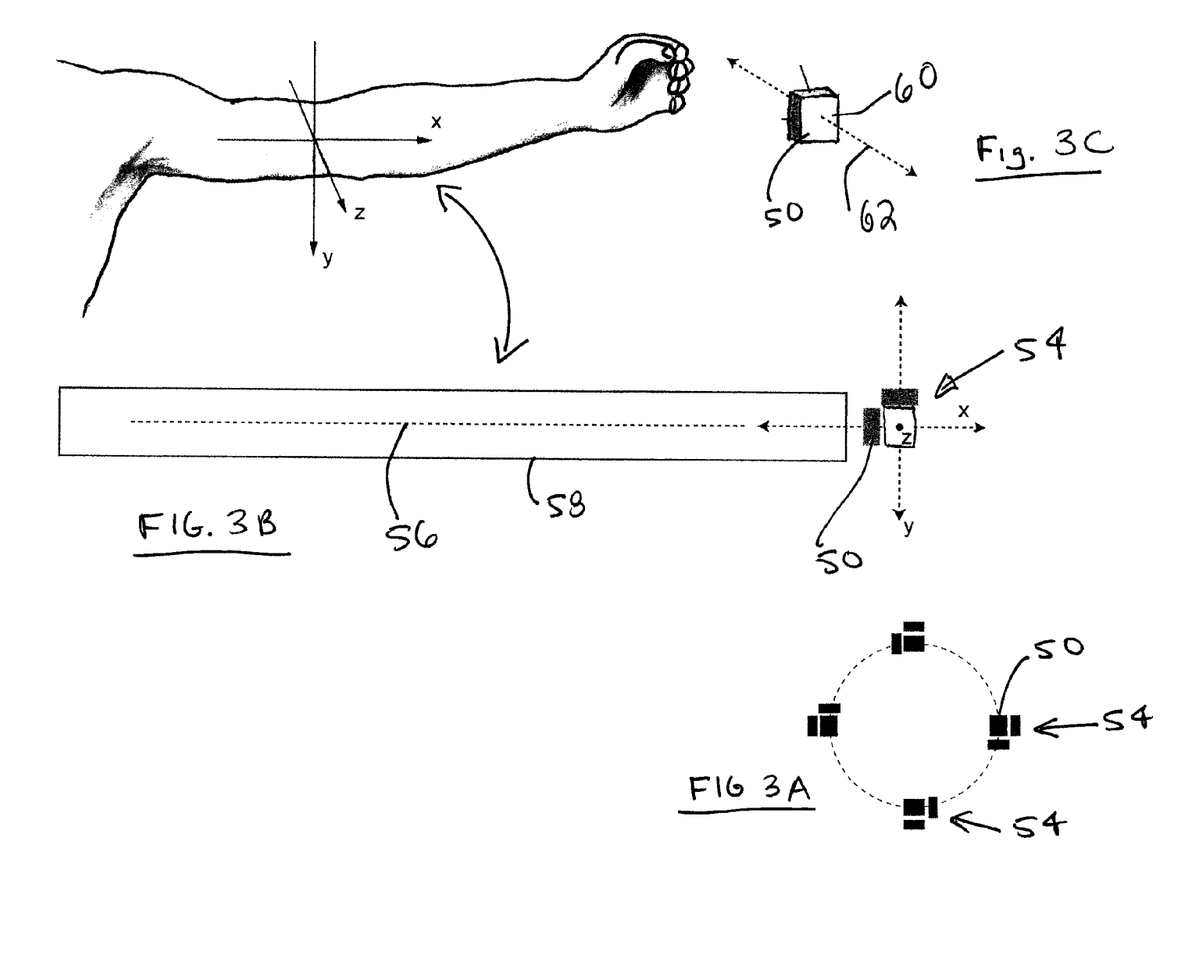
FIGS. 3A, 3B and 3C diagrammatically represent clusters of three orthogonally disposed magnetic sensors and their orientation with respect to the longitudinal axis of a humerus.

The axial placement of sensors 50 vis-á-vis magnet 40 is illustrated diagrammatically in FIGS. 3A and 3B. FIG. 2A thus illustrates an axially displaced positioning of the plane of the magnet sensors vis-á-vis magnet 40. This is currently the preferred approach. Also, although the axial displacement will preferably be about 2 to 3 cm, the actual ideal spacing of the plane of the sensors from the magnets may be determined on a case-by-case basis. Alternatively, the sensors may be positioned so that the magnet lies in the plane of the sensors, which would be a "circumferential" placement. Appropriate adjustment in the control algorithm of the microprocessor will be made depending on whether the axially displaced configuration of FIG. 2A or the circumferential placement of FIG. 2B is used.

While the number of sensors used may vary, it is currently preferred that the sensors be arranged in four clusters 54 of three orthogonally disposed sensors as illustrated in FIG. 2A. It is also preferred that Hall-effect sensors be used although other sensors that may be used including anisotropic, magnetoresistive and giant magnetoresistive sensors, and fiberoptic magnetometers.

Each Hall-effect or other sensor measures the magnetic field vector orthogonal to its face 60 and along measurement axis 62. (FIG. 3C.) Therefore, the sensors are aligned as shown in FIG. 3B (where the Z axis is directed perpendicularly to the page) to measure the magnetic field along the three axes—X, Y, and Z—defined anatomically (see anatomical coordinate system in top portion of FIG. 3B), with the X axis being aligned with the longitudinal axis 56 of the bone 58 (the distal-proximal axis), and Y (medial-lateral) and Z (anterior-posterior) axes perpendicular to one another and orthogonal to the z axis. Because rotation about the X-axis is the desired measurement, it simplifies microprocessor calculations to have the field vectors calculated along the axes in the correct coordinate system. Otherwise, coordinate transformations may be made as appropriate.

In a less preferred embodiment of the invention only two clusters of magnetic sensors may be used to determine the rotation and orientation of the magnetic field associated with magnet 40. However, four clusters are preferred to insure that the magnetic field of the magnet can be sensed by at least two sensor clusters regardless of where the magnet travels within the soft tissue of the residual limb.

In order for the sensor clusters to isolate the rotary motion at a particular instant, it is preferred that they know where the bone is located at that instant which gives rise to the need for sensing translation of the magnet. This translation, of course, may be in three dimensions, whereas the rotation is along a single axis. The sensors thus calculate at each instant in time what is the position in three dimensions of the embedded magnet permitting the determination of the direction and degree of rotation of the residual bone along its longitudinal axis. In other words, preferably the system keeps track of translation of magnet 40 to make sure that the rotation determination is correct at all times.

The outputs of sensors 50 are analog output voltages that may be amplified with a high-performance instrumentation-amplifier and processed with conditioning circuitry. The outputs are routed to a control loop with a microprocessor 64 and a motor controller 66. For example, a PIC 18f4520 microcontroller may be used. The microprocessor may use a proportional integral derivative (PID) controller which will send motion signals to the prosthetic rotator 68 of the superior limb prosthesis. One such commercially available prosthetic rotator (which is currently used with myoelectric controls) is the 10S17 Otto Bock Electric Wrist Rotator made by Otto Bock of Minneapolis, Minn.

Microprocessor 64 will be mounted to the prosthesis. While there is no criticality in where the microprocessor is located in the prosthetic arm, the location will depend on the level of amputation and which prosthetic components are used. In a transhumeral amputee the microprocessor can be located in the distal upper arm or in the forearm as shown. For a transradial amputee it would be located in the distal forearm, proximal to the prosthetic wrist. For a transfemoral amputee it would be located proximal to the knee joint but distal to the end of the socket. In all cases, it should be placed wherever it is most clinically appropriate.

A data acquisition (DAQ) device such as a National Instruments NI USB-6218 may be used to collect data from the sensors. This device may be configured, for example, using 16 differential inputs with a sample rate of 1000 Hz. The differential configuration helps eliminate common-mode noise from the signal. MATLAB (available from the MathWorks of Natick, Mass.) was used to perform all aspects of the data acquisition and computation.

Magnetic fields from sources other than magnet 40 that exist around a subject may interfere with the magnetic field sensors in the prosthesis. The largest likely source would be magnetic interference from the permanent magnet motor of an elbow actuator. The interference may be attenuated and effectively eliminated as a source of meaningful error in rotation by applying a shield cap to surround the magnet and magnetic sensors such as by positioning it over the outer surface 70 of the outer socket. Preferably the shield cap will be made of a super high magnetic permeability material such as Permalloy 80 which is available from Electronic Products International of Ashland, Oreg. Permalloy 80 is a nickel-iron-molybdenum alloy which provides high initial and maximum magnetic permeabilities and minimal core losses at low field strengths making it an effective magnetic shielding material. Also, a cap covering the distal end of the residual limb and extending further proximally may be used to further reduce outside magnetic interference. Alternatively, a coating of high magnetic permeability material may also be used.

FIG. 2 depicts an arm prosthesis 70 applying generally the above structures and principles in instantaneously converting rotation of the radius 72 into rotation of a prosthetic hand 74. Rotation of the radius (and ulna 76) is caused by muscles in the forearm attached to the elbow and to the radius and ulna.

Figure 4:
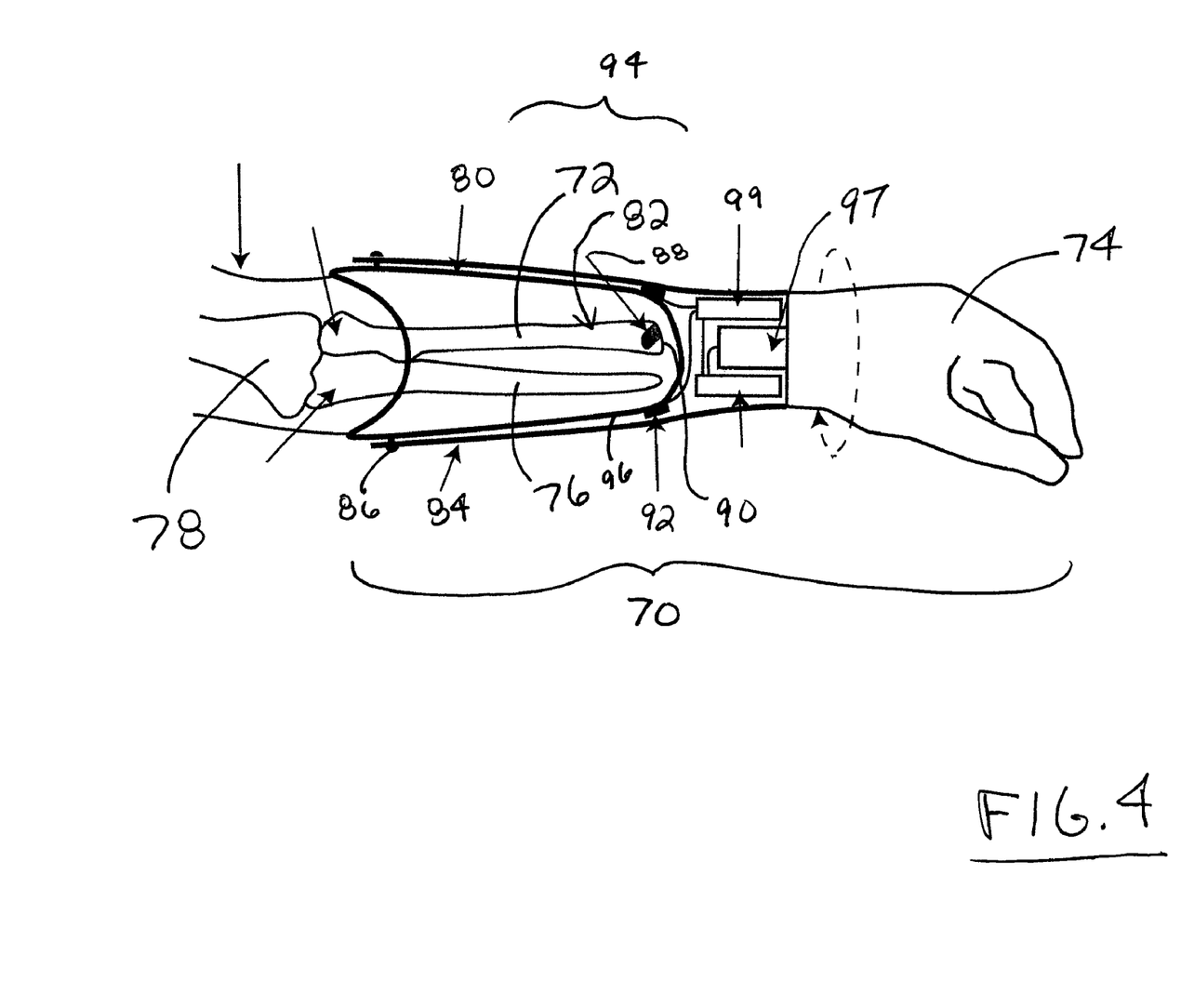
FIG. 4 is a diagrammatic representation of an arm prosthesis attached to a residual radius.

Thus, an inner socket 80 is fit intimately to the residual limb. Then an outer socket 84 is mechanically attached to the inner socket by conventional attachment means such as bolts 86. A permanent magnet 88 with a fixed magnetic field is mounted adjacent the distal tip 90 of radius 72. The magnetic axis of the magnet is generally perpendicular to the longitudinal axis of the residual radius in which it is mounted.

Magnetic field sensors 92 are disposed about magnet 88 to sense the rotation of the magnetic field of the magnet as the amputee rotates radius 72 within compliant soft tissue envelope 94. The magnetic field sensors are mounted to the outer surface 96 of the inner socket. The outputs of the sensors are routed to a control loop including a microprocessor 98 and motor controller 99 which sends motion signals to a prosthetic rotator 97 which is attached to prosthetic hand 74.

Rotation at the knee is analogous to humeral rotation. Little to no rotation is actually available at the knee joint itself. Instead, rotation at the knee (referred to as femoral rotation) is generated at the hip joint and transferred to the knee via rotation of the femur. With a transfemoral amputation, the femur is still able to rotate, but this rotation is lost as the bone moves freely within the soft tissue. Little to none of this rotation is transmitted to the outer socket through the soft tissue and skin. However, the rotation of the femur is sensed naturally by the amputee via the intact proprioceptive pathways of the hip joint (muscle spindles, golgi tendon organs, and joint capsules). Thus, a magnet may be located at the distal end of the femur in conjunction with an appropriately structured leg prosthesis using the other key operative elements of magnetic sensors, etc. of the devices of FIGS. 1 and 4 as discussed above. In this way the present invention can also achieve prosthetic knee rotation.

EXAMPLES

The following examples further illustrate the invention but, of course, should not be construed as in any way limiting its scope.

Example I

A simulation study as described below was conducted with finite element models of the upper arm to demonstrate details of the approach of the invention in sensing the rotation of a residual humerus. Further details of the study and related implementation of the invention are described in Li G, Kuiken T. A. "Modeling of Prosthetic Limb Rotation Control by Sensing Rotation of Residual Arm Bone," *IEEE Trans Biomed Eng.*, 55(9): 2134-2142, September 2008.

While the invention also can be used for controlling pronation and supination of the forearm in a below-elbow amputee, the upper arm was chosen in the study due to its greater symmetry allowing a simpler model, and because the upper arm is larger in size than the forearm, which would attenuate the magnetic fields so that a sensitivity analysis is more relevant. This analysis included the effects of arm size, magnet dimensions, relative position of the magnet to magnetic sensors, orientation of the magnet relative to the limb axis, displacement of the magnetic sensors on the magnetic field and external magnetic interference on the distribution of magnetic field of the magnet.

Using finite element analysis, an upper arm with a residual humerus bone, represented as concentric, coaxial cylinders were modeled. Then, a magnet inserted into the distal portion of the bone was modeled. The simulated magnetic field values at various locations on the surface of the model arm were then calculated under various conditions.

The best case scenario was considered to be when the humerus was positioned exactly in the center of the residual arm. For an average limb size (radius=50 mm) with an implanted magnet having a residual magnetic flux density of 11 KGs, the peak-to-peak magnetic field strength was found to be about 35 G over 90 degrees. This provided a positioning resolution of about 0.39 G per degree rotation of residual humerus.

A sensitivity analysis of limb and magnet sizes was performed to assess the range of field strengths that would be produced on the arm surface. In the worst case that a given-size magnet was implanted into the residual humerus in a big upper arm with a radius of 60 mm (arm circumference≈377 mm), the magnet still generated a magnetic field change rate of about 0.22 G per degree humerus rotation in the y-direction on arm surface. Using a Hall-effect magnetic sensor such as A3515 (Allegro MicroSsystems, Inc.) to detect the magnetic field, this would produce an analog voltage change rate of about 1.1 mV per degree humerus rotation. While this is believed to be adequate for signal amplification, a larger magnetic sensor could be used for higher quality signals. With a given magnet size, a smaller limb will have larger magnetic fields on the limb surface. Similarly, smaller diameter magnets will produce smaller magnetic fields. The sensitivity analysis serves as a guide for determining the needed magnet size with respect to the limb size and bone diameter. The data indicate that considerably smaller magnets could be used, if needed, with smaller residual limbs and smaller bones.

In practical application the distal humerus and magnet may not be perfectly located in the middle of the residual limb. When wearing a prosthetic socket, the distal humerus will move anteriorly with arm flexion, laterally with abduction, posteriorly with extension and medially with adduction. How far the off-center depends on how well the humerus is secured with myodesis and myoplasty, the thickness of the overlying soft tissue layer (fat) and the loads on the socket. The simulation results showed that when the magnet was off-center less than 5 mm (corresponding to about 2-pound load on the arm), the magnetic field distribution over the arm surface retained a similar sinusoidal pattern and the peak-to-peak strength of the Y-direction component of the magnetic field had a 4.5-G increase over 90 degrees. When the distal humerus was displaced greater than 15 mm (corresponding to about 5.2-pound load on the arm), the distribution of the Y-direction component became a triphasic pattern and its peak-to-peak strength increased greatly to 43 G for Y-direction shift and 21 G for z-direction shift. Humeral displacement causes much greater magnetic fields to be produced at the limb surface and the loss of the simple sinusoidal pattern. An array of surface sensors as illustrated in FIG. 1 and discussed above will accurately determine the vector of the magnetic field regardless of where the distal humerus is positioned within the residual limb. The magnet is located proximally to the sensor and is spaced from the plane of the sensor. The number of sensors will affect magnetic vector angle resolution. Sensors may be desirable in more than one plane to accommodate the residual limb slippage in the socket.

Other magnetic fields that exist around a subject could interfere with the magnetic field sensors in the prosthesis. The largest likely source would be the magnetic interference from the permanent magnet motor of an elbow actuator. An analysis of the performance of a shield cap surrounding the distal end of the residual limb in accordance with the invention in attenuating magnetic interference was carried out by simulation. The strength of the magnetic interference displayed a plateau distribution around the prosthetic arm surface demonstrating that the interference of the magnetic fields was effectively attenuated by a shield cap positioned at the distal end of the residual arm by over 99%. This magnetic interference (using the cap) would bias the magnetic field sensors causing a positioning error of less than 0.2 degrees for prosthetic humeral rotation control with respect to the positioning resolution of 0.39 G/degree described above for an average sized arm with an 11-KGs magnet. Even able-bodied people can not accurately position their arm with a 0.2-degree resolution. Thus this 0.2-degree positioning error would not significantly affect the accurately positioning of a prosthetic arm.

However, as noted above, the use of smaller magnets may be more adversely affected by such interference. Therefore, caps covering the distal end of the residual limb and extending further proximally may be used to further reduce outside magnetic interference. Also, the cap may be in the form of a metal layer or coating on the outside of the prosthetic arm preferably extending on the prosthetic arm along the entire socket. The socket depth, of course, is determined on a case by case basis at the design and fitting of the prosthesis and is dependent, inter alia, on the length of the residual limb. Also, dynamic magnetic interference from the motor and other ambient time-varying magnetic fields could be further attenuated with a low pass filter. Since the reasonable physiological maximum speed of wrist rotation is about 2 hertz, the low pass filter preferably will cut off frequencies of about 5 hertz.

Example II

Based on the modeling and simulation performed in Example 1, a further study was carried out to implement working physical models of the system for both transradial and transhumeral amputees. The number of sensors required to uniquely determine the location and orientation of the magnet in the distal end of the residual humerus was examined, and various algorithms for tracking a magnet's translation and orientation in space were evaluated using computer simulations. The algorithm with the best performance was then implemented on working physical models of the system. The physical models were used to determine the overall error in the system caused by translations of the magnet in three dimensions, offsets in the position of the magnet within the residual bone, and interference from external magnetic fields.

Methods

A. System Characterization

For both applications—transradial and transhumeral—the X-axis was taken as along the length of the limb, with positive sense facing distally. The Y-axis was the anterior—posterior axis, with the positive sense facing anteriorly. Similarly, the Z-axis was taken as the inferior—superior axis, with the positive sense facing superiorly. Computationally, the movements of the magnet were described by the parameters $M_x$, $M_y$, $M_z$ and $B_x$, representing the location of the center of the magnet in three dimensions and the rotation of the magnet about the x-axis. Rotations about the Y and Z axes were neglected, as these movements were considered to be constrained by the ball-and-socket shoulder joint on the proximal end, which allows rotation and no translation, and by the prosthetic socket on the distal end, only allowing movement within the soft tissue. The parameters were chosen based on the feasibility of implementation in a physical model.

B. Computational Model

1) Modeling: A simulation was developed in MATLAB 8.0 (Mathworks) to model the 3-D vector field produced by a permanent magnet. Two assumptions were made in modeling the magnetic field: (1) the field was generated from an ideal dipole magnet characterized by its dipole moment and (2) all field strengths pertain to far-field measurements. The magnet was placed in a spherical magnet coordinate system (MCS) with the axis of magnetization along the z-axis. A form of Maxwell's equations describing the field of a magnetic dipole in the MCS ($\vec{v}$) as a function of the distance ($\|\vec{v}\|$) from the center of the magnet to the sensor, the angle ($\theta$, in radians) between the sensor vector ($\vec{v}$) and the z-axis, and the angle ($\theta$, in radians) measured from the y-axis between the projection of the sensor vector on the xy-plane governed the resulting magnetic field (Equation 1). The permeability of free space ($\mu_0 = 4\pi \cdot 10^{-7}$ N/A$^2$) and the magnetic dipole moment (m) were constant values.

$$\vec{B} = \begin{bmatrix} B_r \\ B_\theta \\ B_\phi \end{bmatrix} = \frac{\mu_0 m}{r^3} \begin{bmatrix} 2\cos\theta \\ \sin\theta \\ 0 \end{bmatrix} \quad (1)$$

These magnetic field equations were then transformed into a corresponding Cartesian coordinate system (Equation 2) in order to be congruent with the MCS of the system.

$$\vec{B} = \begin{bmatrix} B_x \\ B_y \\ B_z \end{bmatrix} = \begin{bmatrix} (B_r\sin\theta + B_\theta\cos\theta)\cos\phi \\ (B_r\sin\theta + B_\theta\cos\theta)\sin\phi \\ B_r\cos\theta - B_\theta\sin\theta \end{bmatrix} \quad (2)$$

2) Sensor Placement: The investigation of sensor placement involved first determining the maximum distance that gave sufficient signal strength, given the sensor noise. Secondly, the minimum number of sensors necessary for robust magnetic field measurements irrespective of magnet position were determined. This investigation was done using Nelder-Mead optimization (MATLAB Optimization Toolbox) for the dipole equations, solving for $M_x$, $M_y$, $M_z$, $\beta_x$ for a range of initial guesses. For transhumeral subjects, the average mid-arm diameter is 10 cm. Therefore, sensors located circumferentially would have an average distance to the magnet of over five centimeters. However, if the sensors were placed distally to the end of the residual limb, this would take advantage of the relatively small distance between the distal residual humerus and the distal end of the residual limb. This distance is approximately three centimeters. For transradial subjects, the circumferential geometry may be more appropriate; however, the analysis considered the transhumeral case. With these known aspects of sensor location, it was determined how many sensors were required to provide a unique solution, as well as a convenient geometry for the algorithms to traverse.

3) Algorithms: Two optimization algorithms were initially evaluated in order to more quickly and accurately predict the magnet's position and orientation: Gradient Descent and the Newton Method. Both methods use the gradient and curvature of a surface to quickly navigate to local minima. Thus, bone rotation was discerned by matching the Hall-effect sensor measurements (input to the microprocessor via a data acquisition card) to theoretical values for different magnet positions and orientations (calculated using a dipole approximation) with an optimization routine. A low-resolution look-up table was generated from the simulated magnetic field distributions of a dipole at different locations and orientations. A cost function was derived from the sum of the squared errors between the actual field measurements taken by the sensors and the simulated field values; the cost function was plotted over the four degrees of freedom (x, y, and z, and rotation about the x axis) to generate an error surface. The closest approximation of the actual position and orientation of the magnet lay at the minimum of the error surface. To get a more accurate prediction of the magnet location and angle, this approximation was used as an initial guess for implementing the Gradient Descent or Newton method of optimization. (The Newton method is characteristic of using the gradient and curvature of a surface to quickly navigate to a local minima). After the first solution was obtained, it was used as an initial guess for the next prediction for the Gradient Descent or Newton algorithm; typically, less than five iterations were necessary to determine the solution. The predicted magnet orientation was used as the reference or input to the motor control loop (which consisted of a microprocessor and H-bridge). The motor encoder data was sent back to the microprocessor where it was used in a PID control scheme.

4) Comparison Tests: In order to determine the feasibility of each optimization algorithm, we determined tests that may be used for comparison. The algorithms were judged with respect to the general determination of magnet position and orientation and their ability to track a simulated magnet trajectory in time-space.

C) Physical Model

Based on the results from the computational model, the sensor number and placement were chosen and the Newton algorithm was chosen for implementation on the physical model.

1) Construction of Physical Upper Arm Model: A cylindrical neodymium-iron-boron (NdFeB) rare earth magnets with a diameter of 6.35 mm and a length of 19.05 mm were used. For this magnet, the residual inductance (Br) was 13.2 kG and the grade was N40. The size was dictated by the ability to fit within the residual humerus once encased within a biocompatible material. Titanium was chosen as the material to encase the magnet. The relative magnetic permeability of the titanium was 1.00005 at 1600 A/m.

Figure 5:
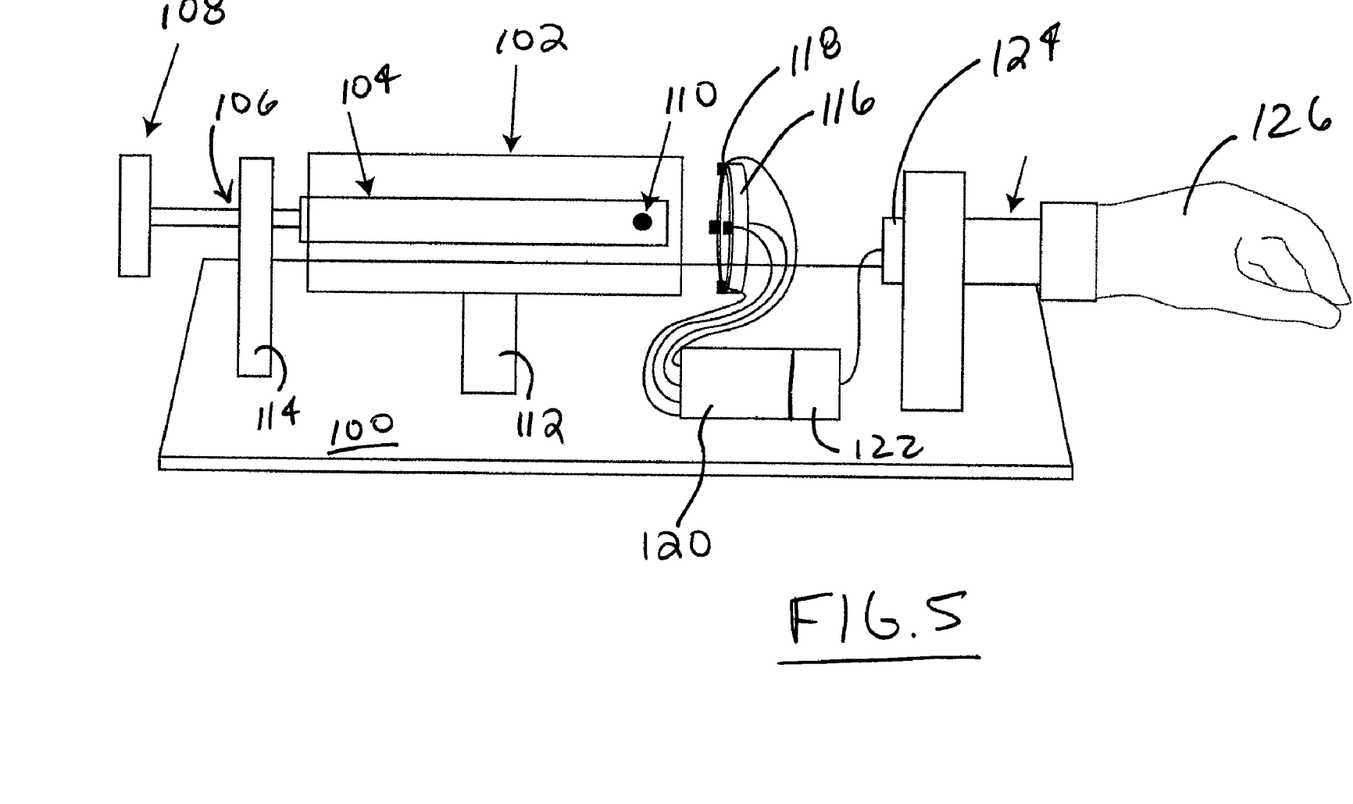
FIG. 5 depicts an experimental setup employed in Example 2.

The model arm used is depicted in FIG. 5. It includes a base 100 supporting a model upper arm 102 constructed from a 10 cm inner diameter clear acrylic tube (thickness of 0.25 in.) with the inner-surface of the tube representing the surface of the arm. There was no medium inside the tube because the magnetic permeability of tissue is approximately the same as that of free space. A model humerus 104 was positioned within the model upper arm modeled as a 2.3 cm diameter extruded nylon rod. The nylon rod was mounted in a 1" inner-diameter stainless-steel bearing 106 far from the magnet. A rotation handle 108 was attached to the model humerus to rotate the model humerus within the model upper arm.

An encased magnet 110 was "implanted" at the distal end of the model humerus across its longitudinal axis. The encased magnet was cylindrical in shape so that its magnetic axis was perpendicular to the longitudinal axis of the model humerus. The magnet was threaded into the nylon through a 9.5 mm diameter hole, 1 cm from the distal end of the nylon rod (FIG. 20). A linear stage 112 installed under the acrylic tube provided Y-axis translation. Z-axis translation was addressed with a polypropylene carriage 114 that supported the roller bearing and nylon bone. The radius of rotation ($R_m$) could be changed by screwing the encased magnet through the nylon bone.

A sensor ring 116 was disposed adjacent the end of the model upper arm with the center of the ring on the longitudinal axis of the model humerus and Hall-effect sensors 118 were disposed at 90 degree intervals along the ring so that they were equal distance from the implanted magnet. Each of the Hall-effect sensors was wired to a microprocessor 120 which in turn was connected to a motor controller 122. The motor controller was connected to a prosthetic rotator 124 arranged to rotate a model hand 126.

Sensors 118 were Allegro A3515 linear ratiometric Hall-effect sensors. These sensors had a sensitivity of 5V/1000 Gauss (G) and a working range of −500-500 G with a 5V supply voltage. The sensors had an RMS noise of 400 µV or 0.08 G and a supply current of approximately 7.2 mA at 25° C. The sensor voltage at 0 G was approximately 2.5 V (with a 5.0 V supply), which indicates a ±2.5 V or 500 G range.

Rotator 124 was a Pittman brushed DC motor with a 19.5:1 gearbox and a built-in optical encoder, counting 500 counts per revolution was used, for the prosthetic rotator. This motor allowed accurate position control while maintaining a large range of possible angular velocities.

Microprocessor 120 was a PIC 18f4520 microcontroller. A NI DAQ device (as described below) output an analog voltage indicating a scaled version of the rotation. The PIC read in the analog voltage and used the encoder to match the angle of the motor. The PIC used standard closed-loop control, with a proportional-derivative control scheme.

2) Data Acquisition and Signal Processing: A National Instruments NI USB-6218 data acquisition (DAQ) device was used to collect data from the Hall-effect sensors. The device was configured using 16 differential inputs with a sample rate of 1000 Hz. The differential configuration was used in order to help eliminate common-mode noise from the signal. MATLAB was used to perform all aspects of the data acquisition and computation.

3) Physical Model Testing: In order to quantify the results of the algorithm when used with the physical model, the predicted locations were compared with the actual magnet location. To test the errors in when the magnet is translated in the X-direction, the magnet was located in the center at 0° and slowly moved in the X-direction. X-translation is defined as the sensors moving forward in the X-axis. This is analogous to the socket slipping off the amputee. The system is restricted to getting closer than approximately −25 mm to the sensors due to the relative position of the sensors and the magnet within the bone. Similarly, the errors associated with Y and Z translations were tested. In each case the magnet was oriented at 0° and translated through the workspace.

4) Construction of Residual Forearm Model: A transradial model generally corresponding to the diagrammatic illustration of FIG. 4 was also developed in order to observe a physiologic representation of the proposed control method. The physiologic motion of forearm pronation and supination was recreated using a flexible joint at the radiohumeral joint while fixing the ulnohumeral joint. The resulting motion—rotation and translation of the radius over the ulna—accurately modeled normal forearm rotation. The bones of the forearm were shortened to 15 cm, typical of an adult male mid-length transradial amputation. A Neodymium-Iron-Boron magnet was implanted into the distal radius. The shape and size of the radius dictated a maximum magnet length of 12.70 mm; the cylindrical magnet had the same diameter (6.35 mm) as the magnet used in the upper arm model of FIG. 4. A molded prosthetic socket was fabricated to fit an average patient with a mid-length transradial amputation. The residual bones were suspended inside the socket such that forearm rotations were possible by turning a handle connected to the radius. As in the upper arm case, soft tissue was not modeled. Four 3-axis Hall-effect sensors were mounted around the circumference of the prosthetic socket, 10 mm proximal to the magnet. The relative proximity of the magnet to the surface of the socket permitted a circumferential sensor array instead of an array at the apex of the socket. Although this model acted as a working physiologic demonstration of the system; the results reported below are from the upper arm model testing.

Results

A) Computational Results

The Newton method was the currently most effective and computationally efficient method of determining magnet orientation. During computational testing, this algorithm followed a simulated magnet position and orientation trajectory with an error of less than 1° for 100% of the trajectory. Furthermore, there was only a 2.7% reduction of accuracy upon introducing a ±0.16 G random noise term into the sensor equations, indicating that the algorithm is robust to sensor noise. When tested on the physical model, the algorithm obtained rotational errors less than 5' for the entire workspace, with errors less than 1° when the magnet was approximately centered.

B) Physical Model Results

The residual bone angle was determined with an error of +2° for rotations centered in the arm; an additional 2° error was found for rotations 6 mm off-center. Thus, the resulting system accuracy was within 4° of the actual bone angle, which is nearly the 3-3.5° threshold of conscious joint angle discrimination. Issues of feasibility, such as socket slippage and motor interference, had negligible effects on the system, while surgical misalignment of the magnet, though a potential source of error, can be minimized through use of intraoperative imaging systems. Furthermore, magnetic field interference caused by a DC motor, a piece of forromagnetic material, and magnet identical to the inserted magnet caused less than 1 degree of error in the system's calculation of the implanted magnet's rotation at distances greater than 30 mm from the surface of the arm.

C) Conclusion

This example demonstrates that this application is feasible for both transradial and transhumeral amputees, and that the rotation of the residual bone can be robustly measured and transmitted to a prosthetic rotator with the use of four 3-axis Hall-effect sensors, implementation of the Newton optimization algorithm, and a simple PID motor controller. The resolution of the detected and commanded rotation angles are less than the error in rotation that is physiologically noticeable. The error in the system that can be caused by reasonably expected magnetic field interference is minimal.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A prosthetic limb for instantaneously converting residual bone rotation into rotation of a portion of the prosthetic limb comprising:
    a permanent magnet having a magnetic field for mounting adjacent to the distal end of the residual bone;
    a plurality of magnetic sensors disposed about the magnet for generating data indicative of changes in the magnetic field produced by rotation of the residual bone and magnet;
    a motor driven prosthetic rotator for rotating the limb portion, and
    a microprocessor programmed to analyze the data indicative of the changes in the magnetic field and to control the prosthetic rotator in response to the data to thereby convert the residual bone rotation into rotation of the limb portion.

2. The prosthetic limb of claim 1 in which the residual bone is a humerus and the limb portion is a prosthetic arm.

3. The prosthetic limb of claim 1 in which the residual bone is a radius and the limb portion is a prosthetic wrist and hand.

4. The prosthetic limb of claim 1 in which the residual bone is a femur and the limb portion is a femoral portion above the knee.

5. The prosthetic limb of claim 1 in which the magnet is disposed with its magnetic axis perpendicular to the longitudinal axis of the residual bone.

6. The prosthetic limb of claim 1 in which the magnet is disposed with its magnetic axis coaxially with the longitudinal axis of the residual bone.

7. The prosthetic limb of claim 1 in which the permanent magnet is a cylindrical neodymium magnet.

8. The prosthetic limb of claim 1 in which the magnet is hermetically sealed in a titanium metal casing with self-tapping threads formed along the cylindrical outer surface of the casing.

9. The prosthetic limb of claim 1 in which an inner socket is fit over the distal end of the residual bone and the sensors are attached to the inner socket wall.

10. The prosthetic limb of claim 1 the sensors are Hall-effect sensors.

11. The prosthetic limb of claim 1 in which the sensors are arranged in four clusters of three orthogonally disposed sensors.

12. The prosthetic limb of claim 11 in which the sensors are aligned to measure the magnetic field along orthogonal X, Y, and Z axes and the X axis is aligned with the longitudinal axis of the residual limb.

13. The prosthetic limb of claim 1 including a shield cap made from a high magnetic permeability material surrounds the magnet and magnetic sensors.

14. A prosthetic limb for instantaneously converting rotation of the residual humerus into rotation of a prosthetic arm comprising:
- a permanent magnet having a magnetic field for mounting adjacent to the distal end of the residual humerus;
- a plurality of magnetic sensors disposed about the magnet for generating data indicative of changes in the magnetic field produced by rotation of the residual humerus and magnet;
- a motor driven prosthetic rotator for rotating the prosthetic arm; and
- a microprocessor programmed to analyze the data indicative of the changes in the magnetic field and to control the prosthetic rotator in response to the data to convert the residual humerus rotation into rotation of the prosthetic arm.

15. A prosthetic limb for instantaneously converting residual bone rotation into rotation of a portion of the prosthetic limb comprising:
- a permanent magnet having a magnetic field for mounting adjacent to the distal end of the residual bone;
- a plurality of magnetic sensors disposed about the magnet in four clusters of three orthogonally disposed sensors for generating data indicative of changes in the magnetic field produced by rotation of the residual bone and magnet;
- a motor driven prosthetic rotator for rotating the limb portion, and
- a microprocessor programmed to analyze the data indicative of the changes in the magnetic field and to control the prosthetic rotator in response to the data to thereby convert the residual bone rotation into rotation of the limb portion.

16. The prosthetic limb of claim 15 in which the sensors are aligned to measure the magnetic field along orthogonal X, Y, and Z axes and the X axis is aligned with the longitudinal axis of the residual limb.

17. The prosthetic limb of claim 15 in which the residual bone is a humerus and the limb portion is a prosthetic arm.

18. The prosthetic limb of claim 15 in which the residual bone is a radius and the limb portion is a prosthetic wrist and hand.

19. The prosthetic limb of claim 15 in which the residual bone is a femur and the limb is a femoral portion above the knee.

* * * * *